United States Patent [19]

Coy et al.

[11] Patent Number: 4,904,642
[45] Date of Patent: Feb. 27, 1990

[54] THERAPEUTIC SOMATOSTATIN ANALOGS

[75] Inventors: David H. Coy, New Orleans; William A. Murphy, Covington, both of La.; Mark L. Heiman, Indianapolis, Ind.

[73] Assignee: The Administrators of the Tulane Educational Fund, New Orleans, La.

[21] Appl. No.: 312,138

[22] Filed: Feb. 17, 1989

Related U.S. Application Data

[60] Division of Ser. No. 209,883, Jun. 22, 1988, which is a continuation-in-part of Ser. No. 70,400, Jul. 7, 1987, abandoned, which is a continuation-in-part of Ser. No. 10,349, Feb. 3, 1987, abandoned, which is a continuation-in-part of Ser. No. 875,266, Jun. 17, 1986, abandoned, which is a continuation-in-part of Ser. No. 775,488, Sep. 12, 1985, abandoned.

[51] Int. Cl.$^4$ .................. A61K 37/02; C07K 7/26
[52] U.S. Cl. .................... 514/11; 530/311; 514/806
[58] Field of Search .............. 530/311; 524/14; 514/11, 806

[56] References Cited

U.S. PATENT DOCUMENTS

| | | | |
|---|---|---|---|
| 4,282,143 | 8/1981 | Sarantakis | 530/328 |
| 4,291,022 | 9/1981 | Sandrin et al. | 514/11 |
| 4,328,135 | 5/1982 | Sarantakis | 525/54.11 |
| 4,395,403 | 7/1983 | Bauer et al. | 530/311 |
| 4,435,385 | 3/1984 | Bauer et al. | 530/311 |
| 4,485,101 | 11/1984 | Coy et al. | 514/11 |

FOREIGN PATENT DOCUMENTS

| | | |
|---|---|---|
| 0029579 | 6/1981 | European Pat. Off. |
| 0203031 | 11/1986 | European Pat. Off. |
| WO86/1516 | 9/1984 | PCT Int'l Appl. |
| 2095261 | 9/1982 | United Kingdom |

OTHER PUBLICATIONS

Veber et al., Life Sciences, 34:1371–1378 (1984).
Torres-Aleman, Chemical Abstracts 102:160733u (1985).
Schally et al., Proc. Natl. Acad. Sci. USA, 84:7275–7279 (1987).
Siegel et al., Cancer Research, 48:4651–4655 (1988).
Cai, "Synthesis and Evaluation of Activities of Octapeptide Analogs of Somatostatin," Nature, 292:55 (1981).
Lamberts et al., "Potential Role of Somatostatin Analogues in the Treatment of Cancer," European J. of Clin. Invest., 17:281–287 (1987).
Setyono-Han et al., "Direct Inhibitory Effects of Somatostatin (Analogues) on the Growth of Human Breast Cancer Cells," Cancer Research 47:1566 (1987).
Moreau et al., "Therapeutic Advances and Perspectives," Life Sciences, 84:7275–7279 (1987).
Reubi et al., "Somatostatin Receptors in Human Endocrine Tumors," Cancer Research, 47:551–558 (1987).
Murphy et al., Chem. Abstracts 104:28911x (1986).
Cai et al (1985), Proc. 9th Ann. Peptide Symposium Abstr.

Primary Examiner—Delbert R. Phillips
Attorney, Agent, or Firm—Fish & Richardson

[57] ABSTRACT

An octapeptide of the formula:

$$\begin{array}{c} A_1 \quad A_3 \\ \phantom{A}\diagdown \phantom{A} | \\ N-CH-CO-Cys-A_4-D\text{-}Trp-Lys-A_5-Cys-A_7-NH_2, \\ \phantom{A}\diagup \\ A_2 \end{array}$$

wherein each $A_1$ and $A_2$, independently, is H, $C_{1-12}$ alkyl, $C_{7-10}$phenylalkyl, $R_1CO$ (where $R_1$ is $C_{1-20}$ alkyl, $C_{3-20}$ alkenyl, $C_{3-20}$ alkinyl, phenyl, naphthyl, or $C_{7-10}$ phenylalkyl), or $R_2OCO$ (where $R_2$ is $C_{1-10}$ alkyl or $C_{7-10}$ phenylalkyl), provided that when one of $A_1$ or $A_2$ is $R_1CO$ or $R_2OCO$, the other must be H; $A_3$ is $CH_2$-$A_6$ (where $A_6$ is pentafluorophenyl, naphthyl, pyridyl, or phenyl); $A_4$ is o- m- or p-substituted X-Phe (where X is a halogen, H, $NO_2$, OH, $NH_2$, or $C_{1-3}$ alkyl), pentafluoro-Phe, or $\beta$-Nal; $A_5$ is Thr, Ser, Phe, Val, $\alpha$-aminobutyric acid, or Ile, provided that when $A_3$ is phenyl, $A_1$ is H, and $A_2$ is H, $A_5$ cannot be Val; and $A_7$ is Thr, Trp, or $\beta$-Nal; or a pharmaceutically acceptable salt thereof.

11 Claims, No Drawings

THERAPEUTIC SOMATOSTATIN ANALOGS

BACKGROUND OF THE INVENTION

This application is a continuation of co-pending application Ser. No. 209,883 filed on June 22, 1988, which is a continuation in part of Coy et al. U.S. Ser. No. 070,400, filed July 7, 1987, which is a continuation in part of Coy et al. U.S. Ser. No. 010,349, filed Feb. 3, 1987, which is a continuation in part of Coy et al. U.S. Ser. No. 875,266, filed June 17, 1986, which is a continuation in part of Coy et al. U.S. Ser. No. 775,488, filed Sept. 12, 1985.

This invention relates to therapeutic peptides.

A number of somatostatin analogs exhibiting GH-release-inhibiting activity have been described in the literature, including analogs containing fewer than the naturally occurring fourteen amino acids. For example, Coy et al. U.S. Pat. No. 4,485,101, hereby incorporated by reference, describes dodecapeptides having an N-terminal acetyl group, a C-terminal $NH_2$, D-Trp at position 6, and p-Cl-Phe at position 4. (Herein, when no designation of configuration is given, the L-isomer is intended.)

SUMMARY OF THE INVENTION

In general, the invention features an octapeptide of the formula:

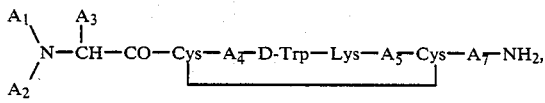

wherein each $A_1$ and $A_2$, independently, is H, $C_{1-12}$ alkyl, $C_{7-10}$ phenylalkyl, $R_1CO$ (where $R_1$ is $C_{1-20}$ alkyl, $C_{3-20}$ alkenyl, $C_{3-20}$ alkinyl, phenyl, naphthyl, or $C_{7-10}$ phenylalkyl), or $R_2OCO$ (where $R_2$ is $C_{1-10}$ alkyl or $C_{7-10}$ phenylalkyl), provided that when one of $A_1$ or $A_2$ is $R_1CO$ or $R_2OCO$, the other must be H; $A_3$ is $CH_2—A_6$ (where $A_6$ is pentafluorophenyl, naphthyl, pyridyl, phenyl, or o-, m-, or, more preferably, p-substituted phenyl, where the substituent is a halogen, $NH_2$, $NO_2$, OH, or $C_{1-3}$ alkyl); $A_4$ is o-, m-, or, more preferably, p-substituted X-Phe (where X is a halogen, H, $NH_2$, $NO_2$, OH, or $C_{1-3}$ alkyl), pentafluoro-Phe, or β-Nal; $A_5$ is Thr, Ser, Phe, Val, α-aminobutyric acid, or Ile, provided that when $A_3$ is phenyl, $A_1$ is H, and $A_2$ is H, $A_5$ cannot be Val; and $A_7$ is Thr, Trp, or β-Nal; or a pharmaceutically acceptable salt thereof.

In the formula given above, the configuration of the molecule at the carbon atom to which $A_3$ is bonded is not given, to indicate that the amino acid residue of which $A_3$ is a substituent can have the D- or L- configuration. In the formula given above, there is a bond shown between the two Cys residues to indicate cyclization; in all of the compounds of the invention there is such cyclization, but the Cys-Cys bond lines are omitted for convenience.

Preferred compounds of the invention include D-β-Nal-Cys-Tyr-D-Trp-Lys-Val-Cys-Thr-$NH_2$; D-Phe-Cys-Tyr-D-Trp-Lys-α-Aminobutyric acid-Cys-Thr-$NH_2$; pentafluoro-D-Phe-Cys-Tyr-D-Trp-Lys-Val-Cys-Thr-$NH_2$; N-Ac-D-β-Nal-Cys-Tyr-D Trp-Lys-Val-Cys-Thr-$NH_2$; D-β-Nal-Cys-pentafluoro-Phe D-Trp-Lys-Val-Cys-Thr-$NH_2$; D-β-Nal-Cys-Tyr-D-Trp-Lys-Val-Cys-β-Nal-$NH_2$; D-Phe-Cys-Tyr-D-Trp-Lys-Val-Cys-β-Nal-$NH_2$; D-β-Nal-Cys-Tyr-D-Trp-Lys-α-aminobutyric acid-Cys-Thr-$NH_2$; D-p-Cl-Phe-Cys-Tyr-D-Trp-Lys-α-aminobutyric acid-Cys-Thr-$NH_2$; and acetyl-D-p-Cl-Phe-Cys-Tyr-D-Trp Lys-α-aminobutyric acid-Cys-Thr-$NH_2$; and D-Phe-Cys-β-Nal-D-Trp-Lys-Val-Cys-Thr-$NH_2$.

In other preferred embodiments, a therapeutically effective amount of the therapeutic compound and a pharmaceutically acceptable carrier substance (e.g. magnesium carbonate, lactose, or a phospholipid with which the therapeutic compound can form a micelle). The most preferred carrier substance is mannitol. Examples of such compositions include a pill, tablet, capsule, or liquid for oral administration to a human patient, a spreadable cream, gel, lotion, or ointment for application to the skin of a human patient in need of the compound, a liquid capable of being administered nasally as drops or spray, or a liquid capable of intravenous, parenteral, subcutaneous, or intraperitoneal administration. The pill, tablet or capsule can be coated with a substance capable of protecting the composition from the gastric acid in the patient's stomach for a period of time sufficient to allow the composition to pass undisintegrated into the patient's small intestine. The therapeutic composition can also be administered in the form of an oil emulsion or dispersion in conjunction with a lipophillic salt such as a pamoic acid. The therapeutic composition can also be in the form of a biodegradable sustained release formulation for intramuscular administration. For maximum efficacy, zero order release is desired. Zero order release can be obtained using an implantable or external pump, e.g., Infusaid TM pump, to administer the therapeutic composition.

The compounds of the invention are active in inhibiting the secretion of GH, insulin, and glucagon. Further, the aromatic lipophilic N-terminal end can provide long-lasting in vivo activity.

Other features and advantages of the invention will be apparent from the following description of the preferred embodiments thereof, and from the claims.

DESCRIPTION OF THE PREFERRED EMBODIMENTS

Structure

The compounds of the invention have the general formula recited in the *Summary of the Invention,* above. They are all octapeptide analogs of somatostatin which have D-Trp at position 4; and optional modifications at positions 3 ($A_4$) 6 ($A_5$) and 8 ($A_7$). It has been found that D-β-naphthylalanine at positions 1 and/or 3; Tyr at position 3; and Val at position 6 are modifications which particularly enhance activity.

The compounds can be provided in the form of pharmaceutically acceptable salts or complexes. Examples of preferred salts or complexes are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid.

Synthesis

The synthesis of one octapeptide follows. Other octapeptides of the invention can be prepared by making appropriate modifications, within the ability of someone of ordinary skill in this field, of the following synthetic method.

The first step in the preparation of D-β-naphthylalanine-Cys-Tyr-D-Trp-Lys-Val-Cys-Thr- NH$_2$ was the preparation of the intermediate tert-butyloxycarbonyl-D-β-naphthylalanine-S-methylbenzyl-Cys-Tyr-D-Trp-N$^\epsilon$-benzyloxycarbonyl-Lys-Val-S-methylbenzyl-Cys-O-benzyl-Thr-benzyhydrylamine resin, as follows.

Benzhydrylamine-polystyrene resin (Vega Biochemicals, Inc.) in the chloride ion form was placed in the reaction vessel of a Beckman 990B peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; (f) 10% triethylamine in chloroform.

The neutralized resin was stirred with Boc-O-benzyl-threonine and diisopropylcarbodiimide (1.5 mmole each) in methylene chloride for 1 h and the resulting amino acid resin was then cycled through steps (a) to (9) in the above wash program. The following amino acids (1.5 mmole) were then coupled successively by the same procedure: Boc-S-methylbenzyl-Cys, Boc-Val, Boc-Ne-benzyloxycarbonyl-lysine, Boc-D-Trp, Boc-Tyr, Boc-S-methylbenzyl-Cys, Boc-D-β-naphthylalanine.

The resin was washed and dried and then mixed with anisole (4 ml) and anhydrous hydrogen fluoride (36 ml) at 0° C. and stirred for 45 min. (one can also use thioanisole, trifluoroacetic acid, and trifluoromethane sulfonic acid at a ratio of 1:90:9, for 6 h). Excess hydrogen fluoride was evaporated rapidly under a stream of dry nitrogen and free peptide precipitated and washed with ether. The crude peptide was then dissolved in 800 ml of 90% acetic acid to which was added I$_2$ in methanol until a permanent brown color was present. The solution was then stirred for 1 h before removing the solvent in vacuo. The resulting oil was dissolved in a minimum volume of 50% acetic acid and eluted on a column (2.5×100 mm) of Sephadex G-25. Fractions containing a major component by uv absorption and thin layer chromatography were then pooled, evaporated to a small volume, and applied to a column (2.5×50 cm) of Whatman LRP-1 octadecylsilane (15–20 μM).

The column was eluted with a linear gradient of 10–50% acetonitrile in 0.1% trifluoroacetic acid in water. Fractions were examined by thin layer chromatography and analytical high performance liquid chromatography and pooled to give maximum purity and if desired, a different salt prepared, e.g., acetate or phosphate. Repeated lyophilization of the solution from water gave 170 mg of the product as a white, fluffy powder.

The product was found to be homogeneous by Hplc and Tlc. Amino acid analysis of an acid hydrolysate confirmed the composition of the octapeptide.

The octapeptides of the invention having the formulae pentafluoro-D-Phe-Cys-Tyr-D-Trp-Lys-Val-Cys-Thr-NH$_2$, D-Phe-Cys-Tyr-D-Trp Lys-α-aminobutyric acid-Cys-Thr-NH$_2$, N-Ac-D-β-Nal-Cys-Tyr-D-Trp-Lys-Val-Cys-Thr-NH$_2$, D-β-Nal-Cys pentafluoro-Phe-D-Trp-Lys-Val-Cys-Thr-NH$_2$, D-β-Nal-Cys-Tyr-D-Trp-Lys-Val-Cys-β-Nal-NH$_2$, D-Phe-Cys-Tyr-D-Trp Lys-Val-Cys-β-Nal-NH$_2$; D-β-Nal-Cys-Tyr-D-Trp-Lys-α-aminobutyric acid-Cys-Thr-NH$_2$; D-p-Cl-Phe-Cys-Tyr-D-Trp-Lys-α-aminobutyric acid-Cys-Thr-NH$_2$; acetyl-D-p-Cl-Phe-Cys-Tyr-D-Trp-Lys-α-aminobutyric acid-Cys-Thr-NH$_2$; and D-Phe-Cys-β-Nal-D-Trp-Lys-Val-Cys-Thr-NH$_2$ were made according to methods analogous to those described above.

Use

When administered to mammals, particularly humans, (e.g. orally, topically, intravenously, parenterally in a sustained release, biodegradable form, nasally, or by suppository), the compounds can be effective to inhibit GH release as well as to inhibit insulin, glucagon, and pancreatic exocrine secretion, and to therapeutically affect the central nervous system.

The compounds can be administered to a mammal, e.g. a human, in the dosages used for somatostatin or, because of their greater potency, in smaller dosages. The compounds of the invention can be used for the treatment of cancer, particularly growth hormone-dependent cancer (e.g., bone, cartilage, pancreas (endocrine and exocrine), prostate, or breast), acromegaly and related hypersecretroy endocrine states, or of bleeding ulcers in emergency patients and in those suffering from pancreatitis or diarrhea. The compounds can also be used in the management of diabetes and to protect the liver of patients suffering from cirrhosis or hepatitis. The compounds can also be used to treat Alzheimer s disease, as analgesics to treat pain by acting specifically on certain opiate receptors, and as gastric cytoprotective compounds for ulcer therapy. The compounds can also be used to treat certain types of mushroom poisoning.

The compounds can also be used to treat diabetes-related retinopathy. The anti-cancer activity of the compounds may be related to their ability to antagonize cancer-related growth factors such as epidermal growth factor.

The compounds can be administered to a mammal, e.g., a human, in a dosage of 0.01 to 50 mg/kg/day, preferably 0.1 to 5 mg/kg/day.

Other embodiments are within the following claims.

We claim:

1. An octapeptide of the formula:

D-X—Phe—[A$^1$-]

—Cys—Tyr—D-Trp—Lys—Val—Cys—L-beta-Nal—NH$_2$[-A$^1$]

wherein X is H, OH, CH$_3$, or a halogen, or a pharmaceutically acceptable salt thereof.

2. The octapeptide of claim 1 wherein X is H.

3. A therapeutic composition capable of inhibiting the release of growth hormone, insulin, glucagon, or pancreatic exocrine secretion comprising a therapeutically effective amount of the compound of claim 1 together with a pharmaceutically acceptable carrier substance.

4. A method of treating a mammal in need of reduction of growth hormone, insulin, glucagon, or pancreatic exocrine secretion comprising administering to said mammal a therapeutically effective amount of the compound of claim 1.

5. The therapeutic composition of claim 3 wherein said composition is in the form of a pill, tablet, or capsule for oral administration to a human patient in need of said compound.

6. The therapeutic composition of claim 3 wherein said composition is in the form of a liquid for oral administration to a human patient in need of said compound.

7. The therapeutic composition of claim 5, said composition being coated with a substance capable of protecting said composition from the gastric acid in the stomach of said human patient for a period of time sufficient to allow said composition to pass undisintegrated into the small intestine of said human patient.

8. The therapeutic composition of claim 3, said composition being in the form of a cream, gel, spray, or ointment for application to the skin of a human patient in need of said compound.

9. The therapeutic composition of claim 3, said composition being in the form of a liquid capable of being administered nasally as drops or spray to a human patient in need of said compound.

10. The therapeutic composition of claim 3, said composition being in the form of a liquid for intravenous, subcutaneous, parenteral, or intraperitoneal administration to a human patient in need of said compound.

11. The therapeutic composition of claim 3, said composition being in the form of a biodegradable sustained release compositon for intramuscular administration to a human patient in need of said compound.

* * * * *

UNITED STATES PATENT AND TRADEMARK OFFICE
CERTIFICATE OF CORRECTION

PATENT NO. : 4,904,642

DATED : February 27, 1990

INVENTOR(S) : David H. Coy et al.

It is certified that error appears in the above-identified patent and that said Letters Patent is hereby corrected as shown below:

Column 1, after the title of the invention, insert as a first sentence and paragraph the following:

--This invention was made in the course of work under a grant or award from the U.S. government; therefore, the U.S. gorvernment has rights in this invention.--

Signed and Sealed this

Third Day of March, 1992

Attest:

HARRY F. MANBECK, JR.

*Attesting Officer*    *Commissioner of Patents and Trademarks*